United States Patent
Tuovinen et al.

(10) Patent No.: US 7,564,363 B2
(45) Date of Patent: Jul. 21, 2009

(54) METHOD AND MEASURING ARRANGEMENT FOR MONITORING THE CONDITION OF A GRINDER STONE OF A PULP GRINDER

(75) Inventors: Olli Tuovinen, Tampere (FI); Risto Karojärvi, Tampere (FI); Juhani Valli, Tampere (FI)

(73) Assignee: Metso Paper, Inc., Helsinki (FI)

( * ) Notice: Subject to any disclaimer, the term of this patent is extended or adjusted under 35 U.S.C. 154(b) by 978 days.

(21) Appl. No.: 11/139,879

(22) Filed: May 27, 2005

(65) Prior Publication Data

US 2005/0276305 A1 Dec. 15, 2005

(30) Foreign Application Priority Data

May 31, 2004 (FI) .................................. 20045199

(51) Int. Cl.
*G08B 19/00* (2006.01)
(52) U.S. Cl. .................... 340/581; 340/584; 241/21; 241/28; 374/153; 451/8; 451/41; 451/48
(58) Field of Classification Search ............... 340/581, 340/584; 73/600; 374/100, 132, 153; 162/232, 162/248; 241/1, 21, 28, 30, 33; 451/5, 8, 451/28, 41, 48
See application file for complete search history.

(56) References Cited

U.S. PATENT DOCUMENTS

| 4,438,598 | A | * | 3/1984 | Wohlmuth | ................ 451/5 |
|---|---|---|---|---|---|
| 4,595,150 | A | | 6/1986 | Aario | |
| 5,125,188 | A | * | 6/1992 | Ogawa et al. | ................ 451/5 |
| 5,727,992 | A | | 3/1998 | Blomqvist et al. | |
| 5,904,457 | A | * | 5/1999 | Suwijn et al. | ............... 409/1 |
| 6,074,088 | A | * | 6/2000 | Oberschmid et al. | ........ 374/153 |
| 6,467,707 | B1 | * | 10/2002 | Williams, Jr. | .............. 241/18 |
| 7,337,672 | B2 | * | 3/2008 | Blake et al. | ................ 73/600 |

FOREIGN PATENT DOCUMENTS

| FI | 74749 | 11/1984 |
|---|---|---|
| JP | 08193879 | 7/1996 |
| SU | 973325 | 11/1982 |
| SU | 1721150 | 3/1992 |

OTHER PUBLICATIONS

Official Action issued in Finnish Priority Appl. No. 20045199 dated Dec. 3, 2004.

* cited by examiner

*Primary Examiner*—Davetta W Goins
(74) *Attorney, Agent, or Firm*—Alston & Bird LLP

(57) ABSTRACT

A method and a measuring arrangement for monitoring the condition of a grinder stone of a pulp grinder. A temperature profile for a grinding surface of the grinder stone is determined substantially along the entire length of the grinder stone, a variable representing at least one piece of temperature data of the grinding surface of the grinder stone is determined on the basis of said temperature profile, and the variable representing said temperature data is compared with a reference variable corresponding to said temperature data. If this variable differs from the reference variable in a predefined manner, the state relating to the condition of the grinder stone is identified as abnormal.

Figure 1:
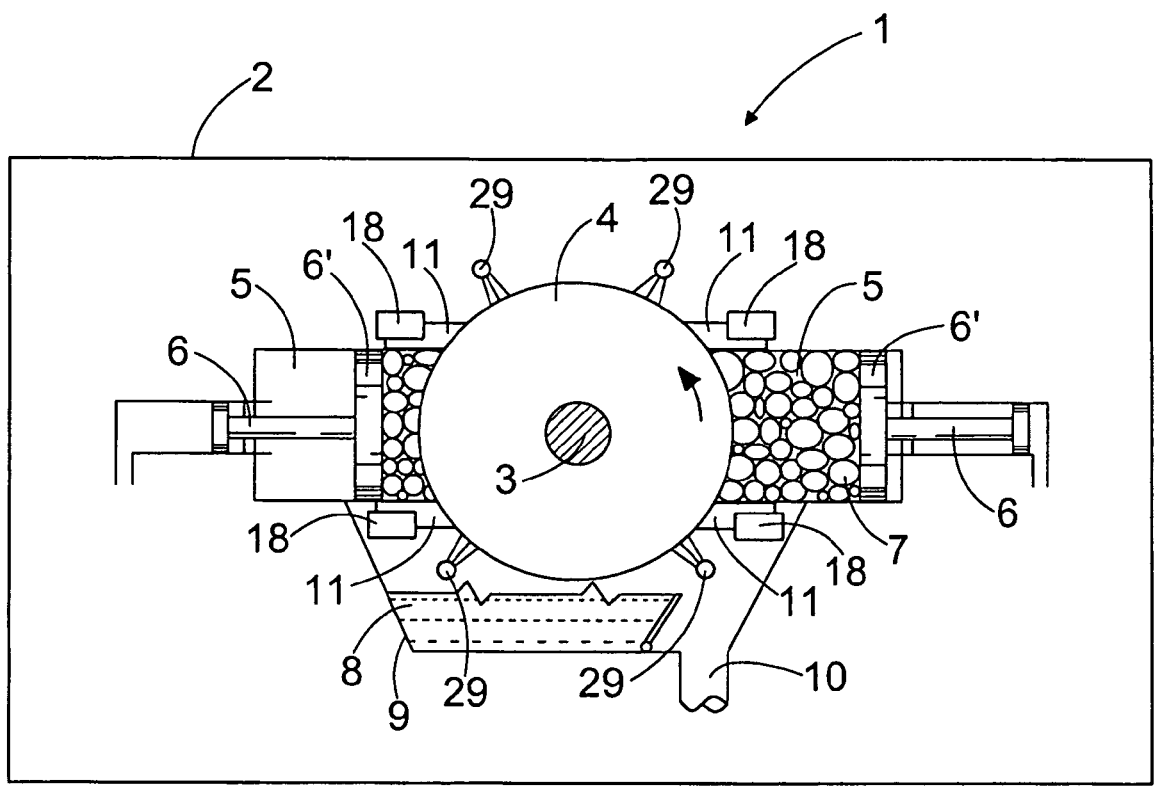

17 Claims, 3 Drawing Sheets

METHOD AND MEASURING ARRANGEMENT FOR MONITORING THE CONDITION OF A GRINDER STONE OF A PULP GRINDER

BACKGROUND OF THE INVENTION

The invention relates to a method for monitoring the condition of a grinder stone of a pulp grinder.

The invention also relates to a measuring arrangement for monitoring the condition of a grinder stone of a pulp grinder.

In pulp grinders, fiber is removed from wood by pressing wooden material, such as blocks of wood, wood chips etc., against the surface of a grinder stone rotating in its longitudinal direction and simultaneously spraying water onto the grinding surface of the grinder stone, whereby, as a result of the grinding effect of the grinder stone and the softening effect of the water, wood fibers are removed from the blocks and form a pulp suspension with the water. The abrasiveness and grinding properties of the grinder stone depend on the surface pattern and grain of the grinder stone. The abrasiveness and grinding properties of the grinder stone change during the grinding, as the grinding surface of the grinder stone wears. As the surface of the grinder stone wears, the properties of fibers produced during the grinding and the properties of the pulp suspension change and thus the usability of the pulp in paper manufacture, for instance, and the properties of the manufactured paper vary.

One reason why the grinding surface of a grinder stone wears are local temperature differences on the grinding surface of the grinder stone, which increase the wear of the grinding surface of the grinder stone by breaking the grinding surface due to local thermal expansions and thus shorten the service life of the grinder stone surface. This problem is familiar to all grinder stones but its consequences are particularly emphasized in connection with grinder stones which have a grinding surface made of ceramics or a ceramic mixture. Local temperature differences can be caused, for instance, so that the grinder stone becomes locally blunt during the normal grinding or if the grinder stone surface is cooled insufficiently. These, in turn, can be caused, for instance, because the grinder stone becomes naturally blunt, jet nozzles spraying water onto the grinding surface of the grinder stone become blocked, a foreign object arrives on the grinding surface or because of the 'vertical chamber' of the grinder, in which the wood is ground endwise.

BRIEF DESCRIPTION OF THE INVENTION

It is an object of the present invention to provide a solution for monitoring the condition of a grinder stone.

The method of the invention is characterized by determining a temperature profile for the grinding surface of the grinder stone substantially along the entire axial length of the grinder stone, determining a variable representing at least one piece of temperature data of the grinding surface of the grinder stone on the basis of said temperature profile, comparing the variable representing said temperature data with a reference variable corresponding to said temperature data and, if the variable representing said temperature data differs from said reference variable in a predefined manner, identifying the state relating to the condition of the grinder stone as abnormal on at least some section of the grinding surface.

The measuring arrangement of the invention is further characterized in that the measuring arrangement comprises means for determining a temperature profile for the grinding surface of the grinder stone substantially along the entire axial length of the grinder stone, means for determining a variable representing at least one piece of temperature data of the grinding surface of the grinder stone on the basis of said temperature profile, means for comparing the variable representing said temperature data with a reference variable corresponding to said temperature data and means for identifying the state relating to the condition of the grinder stone as abnormal on at least some section of the grinding surface, if the variable representing said temperature data differs from said reference variable in a predefined manner.

The essential idea of the invention is that a temperature profile for the grinding surface is determined substantially along the entire length of the grinder stone and a variable representing at least one piece of temperature data of the grinding surface of the grinder stone is determined on the basis of said temperature profile. Furthermore, according to the essential idea, the variable representing said temperature data is compared with a reference variable corresponding to said temperature data and, if the variable representing said temperature data differs from said reference variable in a predefined manner, the state relating to the condition of the grinder stone is identified as abnormal on at least some section of the grinding surface. According to an embodiment of the invention, said state relating to the condition of the grinder stone is the temperature of the grinding surface of the grinder stone. According to a second embodiment of the invention, the temperature profile for the grinding surface of the grinder stone is determined by contact elements arranged in connection with a finger plate closing the gap between the grinding surface of the grinder stone and a grinding chamber and by temperature sensors in connection with said contact elements, whereby the contact elements are arranged to measure the temperature of water and/or a pulp suspension flowing from said gap, representing the temperature of the grinding surface of the grinder stone.

The invention provides the advantage that the risk of damaging the grinding surface of the grinder stone and, in fact, of the entire grinder stone and the grinder itself can be reduced and the service life of the grinder stone can be lengthened considerably. By measuring the temperature of the grinding surface by means of measuring means in connection with a finger plate, the measuring arrangement of the solution can be implemented rather simply.

BRIEF DESCRIPTION OF THE INVENTION

The invention is described in greater detail in the attached drawings, in which

Figure 4:
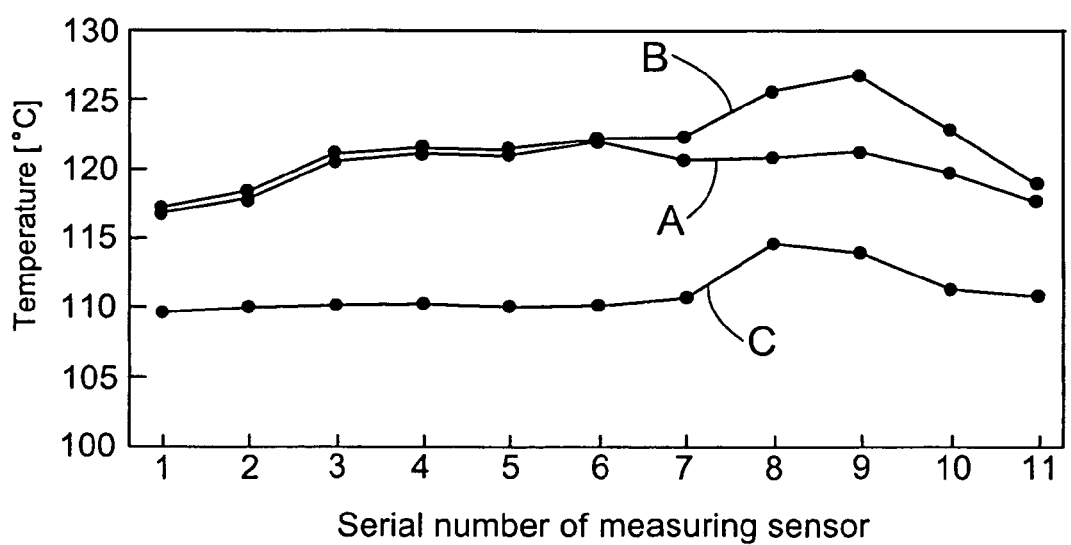
Figure 2:
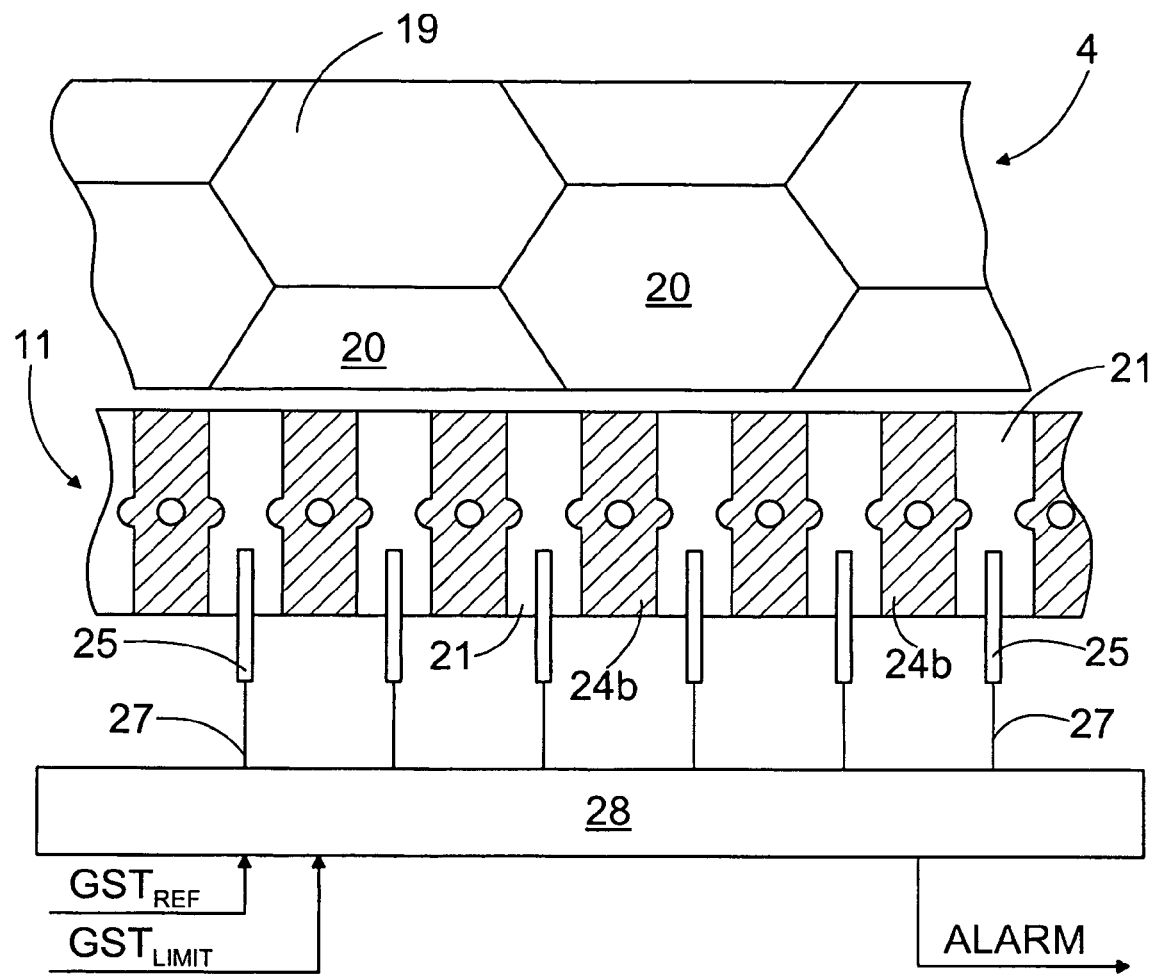
Figure 3:
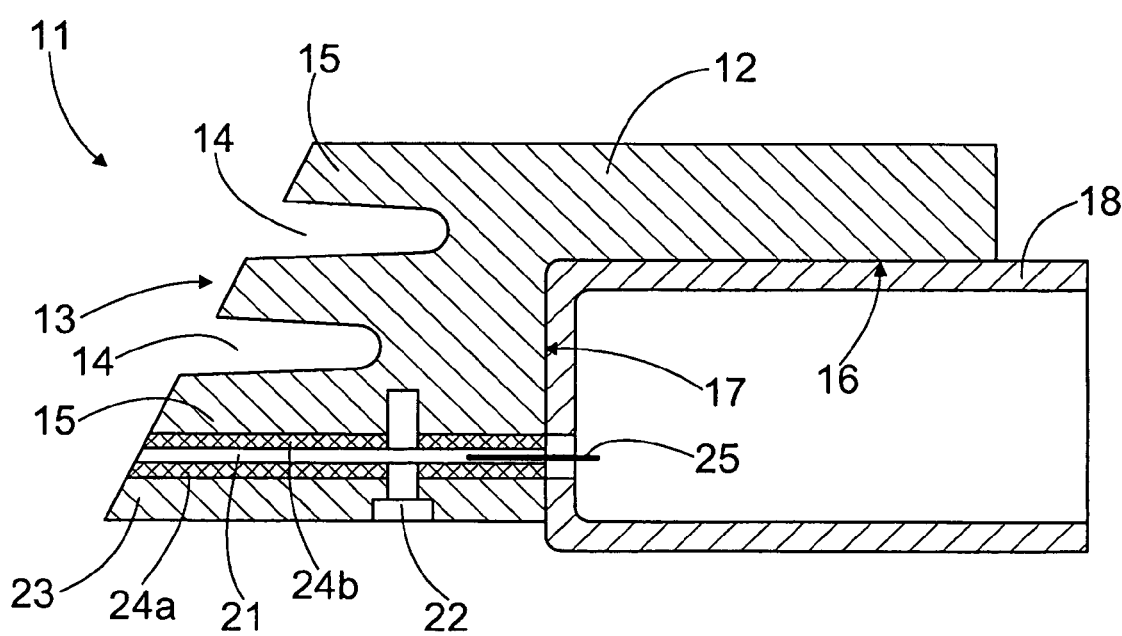
Figure 5:
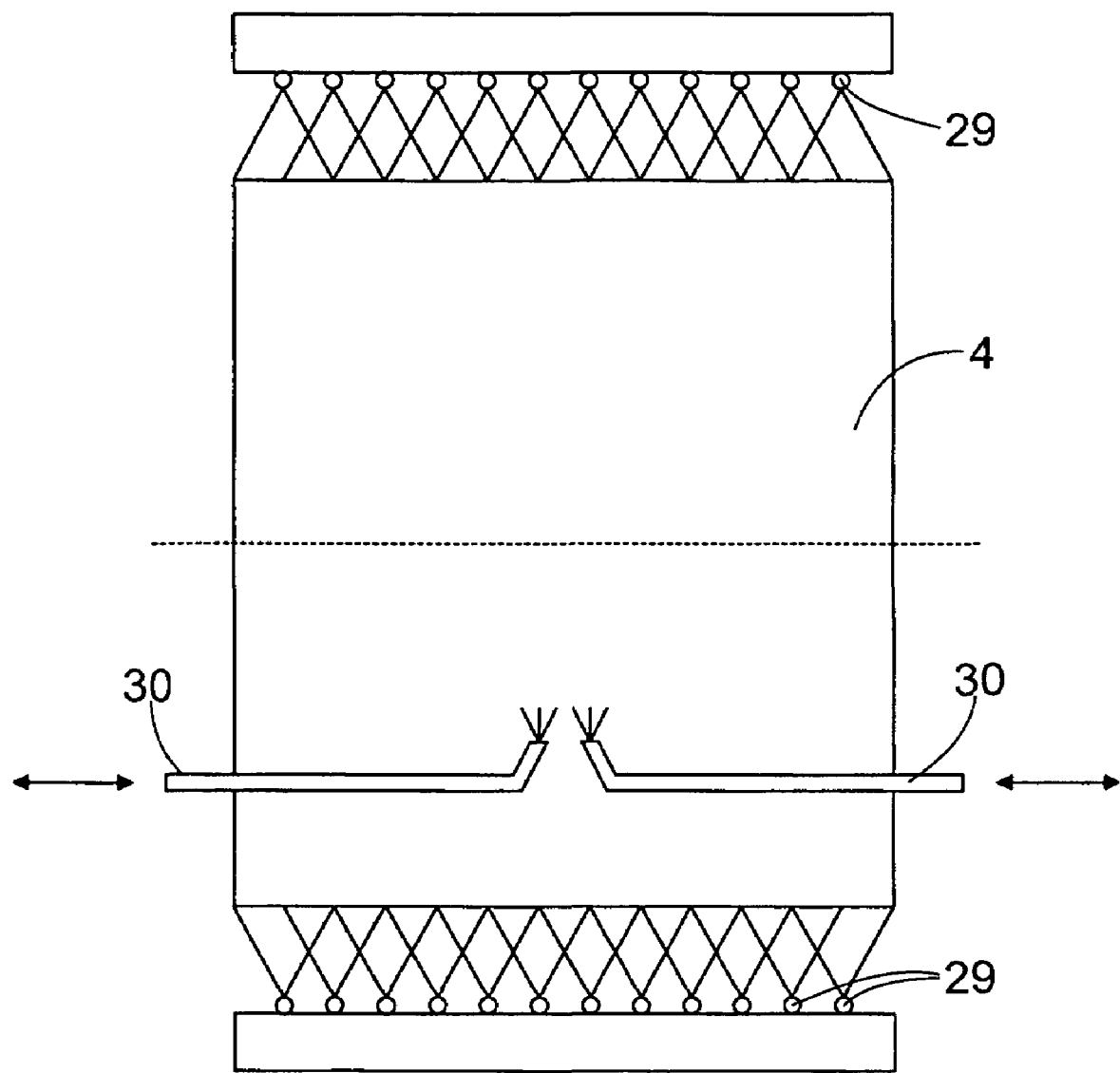

FIG. 1 schematically shows a vertical section of a pulp grinder,

FIG. 2 schematically shows a solution of the invention from above of a grinder stone of the pulp grinder and partly in section, FIG. 3 schematically shows the solution of FIG. 2 from the side and in cross section, FIG. 4 schematically shows temperature profiles measured on the grinding surface of the grinder stone of the pulp grinder, and FIG. 5 schematically shows the grinder stone from above.

For the sake of clarity, the invention is simplified in the figures. Like parts are denoted by the same reference numbers in the figures.

DETAILED DESCRIPTION OF THE INVENTION

FIG. 1 schematically shows a vertical section of a pulp grinder 1, in which the presented solution can be employed.

The pulp grinder 1 of FIG. 1 is a two-chamber piston-loaded pulp grinder 1 comprising a frame 2, schematically illustrated by a box, and a grinder stone 4 rotatably pivoted to the frame 2 and rotated by a shaft 3. A grinding surface 19 (FIG. 2) of the grinder stone 4, which grinds fibers from wood 7, can be made of various materials, but nowadays the grinding surface 19 of the grinder stone 4 is typically made of grinding segments 20 made of ceramics, a ceramic mixture or the like. On the opposite sides of the grinder stone 4 there are two grinding chambers 5 containing wood 7, which is pressed against the grinder stone 4 in a manner known per se by means of pressing pistons 6 and shoes 6' connected thereto. On top or on the side of each grinding chamber 5 there is a feed pocket for a wood charge to be fed to the grinding chamber 5, which is not shown for the sake of clarity. When water is sprayed through washing nozzles 29 during the grinding in a manner known per se, slush pulp 8 is formed from water and wood fibers removed from the wood 7. There are several washing nozzles 29 both in the longitudinal and circular direction of the grinder stone 4. The washing nozzles 29 provide washing water jets, which can also be called cooling water jets. The slush pulp 8 is collected in a basin 9 below the grinder stone 4, from which the slush pulp 8 is further supplied along a discharge pipe 10 to further processing.

FIG. 1 also shows four finger plates 11 supported on the frame of the pulp grinder 1, which are shown in greater detail in FIGS. 2 and 3. FIG. 2 is an illustration from above of the grinder stone 4 of the pulp grinder 1 and a cross section of the finger plate 11, and FIG. 3 shows the finger plate 11 from an end and in cross section. The finger plates 11 are supported on the frame 2 of the grinder 1 by means of support beams 18 at the upper and lower edges of the grinding chambers 5, and they close the gap between the upper and lower edges of the grinding chambers 5 and the grinding surface 19 of the grinder stone 4 so that shives and splinters cannot be taken with the pulp suspension from the grinding zone into the basin 9. The finger plate 11 comprises a lath-like frame 12 extending over the entire length of the grinder stone 4 and having a retaining edge 13 facing the grinder stone 4. The retaining edge 13 of the finger plate 11 of FIG. 3 comprises two longitudinal recesses 14 located between protruding longitudinal retaining ribs 15. The finger plate 11 is placed very close to the grinding surface 19 of the grinder stone 4, e.g. about 1 mm away from the grinding surface 19, so that the water and the pulp suspension can pass between the grinding surface 19 of the grinder stone 4 and the finger plate 11. The retaining ribs 15 are staggered in such a manner that they almost extend to the grinding surface 19 of the grinder stone 4 when the finger plate 11 is mounted on the support beam 18. The frame 12 of the finger plate 11 comprises a longitudinal fastening surface 16 and a support surface 17 perpendicular to the fastening surface 16 for fastening the finger plate 11 to the support beam 18 so that the finger plate is supported on the support beam 18 from two directions. The support beam 18, for its part, is fastened to the frame 2 of the grinder 1 preferably movably in such a manner that, as the grinder stone 4 and the finger plate 11 wear, the finger plate 11 can, from time to time, be adjusted to be as close to the grinding surface 19 of the grinder stone 4 as possible. The finger plate 11 is fastened to the support beam 18 typically by a bolting, which is not shown in the figures for the sake of clarity.

FIGS. 2 and 3 show an arrangement for monitoring the condition of the grinder stone, based on measurement of a temperature profile for the grinding surface 19 of the grinder stone 4. In the solution of FIGS. 2 and 3, a plurality of heat conductive contact elements 21 for determining the temperature of the grinding surface 19 of the grinder stone 4 are arranged in connection with the frame 12 of the finger plate 11. Temperature data $T_i$, wherein i=1 ... n and n is the number of contact elements 21 in the finger plate 11, transferred by each contact element 21 is used for forming a temperature profile $T_{prof}$ for the grinding surface 19 of the grinder stone 4, which is similar to that illustrated by curves A, B and C in FIG. 4. The more contact elements 21 are arranged at the finger plate 11 in the direction of the shaft 3 of the grinder stone 4, the more accurately the temperature profile of the grinding surface 19 can be measured. In order to measure the temperature of the grinding surface 19, the contact element 21 is placed very close to the grinding surface 19 of the grinder stone 4, e.g. about 1 mm away from the grinding surface 19 of the grinder stone 4, whereby the contact element 21 measures in practice the temperature of water/pulp suspension flowing into or out of the gap between the grinding surface 19 of the grinder stone 4 and the finger plate 11, the temperature being almost in a direct relation to the temperature of the grinding surface 19 of the grinder stone 4. Thus, the contact element 21 achieves substantially the same temperature that the grinding surface 19 of the grinder stone 4 has at the contact element 21, although the contact element 21 does not come into contact with the grinder stone itself, but with the mass flowing from the gap between the grinder stone 4 and the finger plate 11. For the manufacturing material of the contact element 21, it is thus important that the contact element 21 is made of a heat conductive material, in which case the temperature changes of the grinding surface 19 can be measured rapidly. For the manufacturing material of the contact element 21 it is also important that the material of the contact element 21 wears more easily than the material of the grinding surface 19 of the grinder stone 4, because, as the finger plate 11 wears during use, also the contact element 21 must wear in order to ensure the proper functioning of the finger plate 11. The contact element 21 can thus be made of copper, for instance.

In the solution of FIGS. 2 and 3, the contact elements 21 are fastened to the frame 12 of the finger plate 11 with bolts 22 or other fastening elements, such as screws, by means of a support lath 23 to be fastened to the frame 12 of the finger plate 11 and two insulating elements 24a and 24b so that the first insulating element 24a is between the support lath 23 and the contact element 21 and the second insulating element 24b is between the contact element 21 and the frame 12 of the finger plate 11. The purpose of the insulating elements, which are not necessary as such, is to prevent heat conduction between the contact element 21 and the finger plate 11 or the support lath 23 so that the temperature of the contact element 21 represents the temperature of the grinding surface 19 of the grinder stone 4 as well as possible. Furthermore, the insulating elements 24a and 24b are arranged to surround the bolts 22, thus preventing heat conduction between the contact element 21 and the bolts 22. The support lath 23, the insulating elements 24a and 24b and the contact elements 21 can be formed in advance into one single structure, which is fastened by the bolts 22 to the frame 12 of the finger plate 11, or the structure can be composed of said separate parts while it is mounted on the frame 12 of the finger plate 11.

The solution of FIGS. 2 and 3 further comprises temperature sensors 25, such as thermoelements, arranged in connection with said contact elements 21 and measuring the temperature of each contact element 21. The temperature sensors 25 thus measure the temperature of the grinding surface 19 of the grinder stone 4 at the contact elements 21 indirectly by means of the contact elements 21. In the embodiment of FIGS. 2 and 3, the temperature sensors 25 are arranged inside the hollow support beam 18 of the finger plate 11 and further in connection with the contact element 21 through an opening 26 in the support beam 18. The temperature data measured by the temperature sensor 25 is supplied along measuring wires 27 further to a data processing unit 28, which can be, for instance, in connection with a control unit of the pulp grinder in the immediate vicinity of the pulp grinder or in a separate control room. The combination of a temperature sensor 25 and a contact element 21 can also be replaced by a mere temperature sensor, if the sensor's own contact element can be arranged to measure the temperature of the grinding surface 19.

In the above, the temperature profile $T_{prof}$ for the grinding surface of the grinder stone 4 was determined by means of the contact elements 21 and the temperature sensors 25. There are other methods for determining a temperature profile $T_{prof}$ as well. The temperature profile can be determined, for instance, by using infrared or laser measuring technology. Since these methods are known per se, they will not be explained in greater detail herein.

On the basis of the temperature data $T_i$ measured by the temperature sensors 25, the data processing unit 28 forms a temperature profile $T_{prof}$ representing the temperature of the grinding surface 19 of the grinder stone 4, like in FIG. 4. On the basis of said temperature profile $T_{prof}$, one or more variables GST representing the temperature data of the grinding surface 19 of the grinder stone 4 are determined, the variable/variables being compared with a reference variable $GST_{REF}$ corresponding to said temperature data and predefined in the data processing unit 28. If the variable GST representing said temperature data differs from said reference variable $GST_{REF}$ in the defined manner, it is stated that the temperature of the grinding surface 19 of the grinder stone 4 differs from its normal temperature at least on some section of the grinding surface. On the basis of this, an alarm signal ALARM, for instance, can be set to indicate an abnormal temperature of the grinding surface 19 of the grinder stone 4 or a temperature differing from the normal one at least on some section in the longitudinal direction of the grinder stone 4. Said alarm signal ALARM can simply cause a visual perception, e.g. a signal light is switched on in the control room, or it can cause an alarm signal in the form of a signal tone or it can be a combination of a signal light and a signal tone. On the basis of the alarm signal, the operator of the grinder 1 can stop the grinder 1, if necessary. The alarm signal ALARM can also automatically stop the grinder 1. Instead of or in addition to the alarm signal, too high a temperature of the grinding surface 19 of the grinder stone 4 and thus the temperature profile of the grinding surface 19 can be changed by normalizing the state relating to the condition of the grinder stone.

The above procedures requiring calculation and comparison are carried out in the data processing unit 28, which can be, for example, a data processing apparatus based on a microprocessor or a signal processor, having a required computing and memory capacity for carrying out the necessary calculation and comparison procedures to be performed by means of software, for instance, and for storing provisional and end results required during the calculation as well as other information, such as one or more reference variables $GST_{REF}$.

FIG. 2 only comprises one data processing unit 28 arranged to determine a variable GST representing at least one piece of temperature data of the grinding surface 19 of the grinder stone 4 on the basis of said temperature profile $T_{prof}$, compare the variable GST representing said temperature data with a reference variable $GST_{REF}$ corresponding to said temperature data and to identify the state relating to the condition of the grinder stone 4 as abnormal on at least some section of the grinding surface 19, if the variable GST representing the temperature data of the grinding surface 19 differs from said reference variable $GST_{REF}$ in a predefined manner. However, it is entirely possible that the variable GST representing at least one piece of temperature data of the grinding surface 19 of the grinder stone 4 is arranged to be determined on the basis of said temperature profile $T_{prof}$ by means of a separate converter, amplifier, calculating unit or computer, and that said variable GST representing the temperature data is arranged to be compared with the reference variable $GST_{REF}$ corresponding to said temperature data by means of a separate amplifier, calculating unit or computer, and that the state relating to the condition of the grinder stone 4 is arranged to be identified as abnormal on at least some section of the grinding surface 19 by means of a separate calculating unit or computer, if the variable GST representing the temperature data of the grinding surface 19 differs from said reference variable $GST_{REF}$ in a predefined manner.

FIG. 4 schematically shows a temperature profile for the grinding surface 19 of the grinder stone 4, measured by means of the contact elements 21 arranged at the finger plate 11, whereby the vertical axis represents the temperature in degrees Celsius and the horizontal axis represents the serial number of the temperature measuring sensor, the serial number corresponding to a certain longitudinal position of the grinder stone 4 and each sensor being at a washing nozzle with a corresponding number. Profile A illustrates the temperature profile for the grinding surface 19, measured on a pilot-sized grinder during normal grinding, i.e. a reference state, when the grinding power is 400 kW. Profile B shows a situation where the washing nozzles with serial numbers 8 and 9 are blocked, which, according to profile B, seems to cause a clear rise in the temperature of the grinding surface 19 at the nozzles with serial numbers 7, 8, 9 and 10. Profile C shows a situation during a chamber change when the washing nozzles 8 and 9 are blocked, the profile C also showing a clear rise in the temperature of the grinding surface 19 at the nozzles 7, 8, 9 and 10.

After the state relating to the condition of the grinder stone 4 is detected to be abnormal on the basis of the temperature measurement and a reason for this is concluded in the above manner, the state can be normalized by eliminating this reason. If the washing nozzle is blocked, it is cleaned or replaced. The problem can also be caused by a faulty directioning of the washing nozzle, in which case the washing nozzle is redirected.

A deviation of the temperature of a section of the grinding surface 19 of the grinder stone 4 from the normal level can be detected in various ways. In its simplest, the temperature $T_i$ measured by each single sensor 25 is compared with a predefined fixed limit value corresponding to the highest allowable temperature of the grinding surface 19 of the grinder stone 4, and if the temperature measured by at least one sensor 25 exceeds said limit value, the abnormal temperature of the grinding surface 19 is identified. Thus, the variable GST representing at least one piece of temperature data of the grinding surface 19 of the grinder stone 4 corresponds to the temperature $T_i$ measured by a single sensor 25 and the reference variable $GST_{REF}$ corresponds to said fixed limit value.

If smaller temperature differences are to be achieved, the solution can be implemented in such a manner that the temperature $T_i$ measured by each single sensor 25 is compared with the mean value of temperatures measured by the sensors 25, whereby the variable GST representing at least one piece of temperature data of the grinding surface 19 of the grinder stone 4 thus corresponds to the temperature $T_i$ measured by a single sensor 25 and the reference variable $GST_{REF}$ corresponds to said mean value of temperatures measured by the sensors 25. In this case, the reference variable $GST_{REF}$ is determined during the same measurement in the data processing unit 28. If the measurement of a single temperature sensor 25 differs from the mean value of temperatures measured by the sensors 25 to a predefined extent, the abnormal temperature of the grinding surface 19 is identified on at least some section of the grinding surface 19.

Furthermore, since the level of the temperature profile depends on the grinding power while the basic form of the profile remains substantially the same regardless of the grinding power, the abnormal deviations of the temperature of the grinding surface 19 can be detected by comparing the shape of the measured temperature profile with the basic form of the temperature profile determined in a normal grinding situation. In this case, the variable GST representing at least one piece of temperature data of the grinding surface 19 of the grinder stone 4 corresponds to the shape of the measured temperature profile, and the reference variable $GST_{REF}$ corresponds to the shape of the temperature profile determined in a normal grinding situation, and the difference between them can be determined, for instance, as the sum of square roots of the difference of the temperature values measured by each single sensor 25 and the temperature values measured by the same sensors in a normal grinding situation. If this sum exceeds a certain limit value representing a predefined number $GST_{LIMIT}$, the temperature of at least some section of the grinding surface 19 of the grinder stone 4 is identified to differ from the normal value. In this case, the shape of the temperature profile can be determined to correspond to the area between the temperature profile of FIG. 4 formed of the measured temperature values and the straight line corresponding to the temperature of 0 degrees.

The solution can also be implemented such that the temperature $T_i$ measured by each single sensor 25 is compared with the temperature values measured by the sensors 25 next to said sensor and, if this measurement differs from the measurement of either of the adjacent sensors by a predefined percentage, for instance, the temperature of the grinding surface 19 of the grinder stone 4 is identified to differ from the normal value on at least this section of the grinding surface 19.

The solution can further be implemented in such a manner that the difference between the highest and the lowest temperature value forming the temperature profile is compared. If the difference of the temperature values increases, it indicates a change of temperature of the grinder stone surface at some point of the measured temperature profile compared to the basic profile of a normal situation. The solution can also be implemented in such a manner that a variable describing the divergence of the temperature values forming the temperature profile is compared. This variable can be mean deviation, variability index or skewness, for instance. If the variable representing divergence increases, it indicates a change of temperature of the grinder stone surface at some point of the measured temperature profile compared to the basic profile of a normal situation. In these both solutions, the temperature of the grinder stone surface has to be measured on at least two points of the grinder stone surface.

The method of the solution for monitoring the condition of a grinder stone allows diminishing the risk of damaging the grinder stones substantially and lengthening the service life of the grinder stone considerably, Due to the solution, the typical service life of a grinder stone 4 of three years can be lengthened by about 20%. Since the temperature variation between the different sections of the grinding surface does not only affect the stone but, when a segment of the grinding surface gets damaged, also finger plates, jet pipes as well as blades and V belts of a slat crusher will break, the repair work causing, at its worst, unplanned several days' interruptions in production, the presented solution can also prevent potential interference to the entire pulp production process.

FIG. 5 schematically shows the grinder stone 4 from above. FIG. 5 also shows washing nozzles 29 as wells as sharpening nozzles 30. The sharpening nozzles 30 provide water sharpening jets. A sharpening jet helps to sharpen the surface of the grinder stone 4 in a manner known per se. The sharpening nozzles 30 are oscillated in the axial direction of the grinder stone according to arrows shown in FIG. 5. If there are two sharpening nozzles 30, each one keeps its own side of the grinder stone 4 sharp and clean.

If a change takes place in the temperature profile, so that one side of the stone begins to heat, it can be stated that there is difference in the operation of the sharpening nozzles 30. The difference may be caused by the fact that one of the sharpening nozzles 30 is blocked or it is directed in the wrong way or that there is a leak either in the pipe system or in connection with one of the sharpening nozzles 30 in the water sharpening system. Thus, after the problem has been detected by the temperature measurement, the sharpening nozzle 30 is cleaned or changed, if necessary, or it is redirected or the leakage in the water sharpening system is fixed.

If a section where the temperature of the grinder stone surface has risen is detected during the measurement of the temperature profile, it can also be due to a blunt part of the stone. If the sharpening nozzle 30 is provided with a positioning function, i.e. it can be controlled to treat a specific part of the grinder stone 4, the blunt part of the grinder stone can be sharpened. Thus, power intake at this part decreases and thus the temperature at this part sinks, too, and the state relating to the condition of the grinder stone is normalized.

The rise in temperature on the surface of the grinder stone 4 can also be caused by a burn streak on the grinder stone surface. In this case, the procedure normalizing the state relating to the condition of the grinder stone is the mechanic removal of this burn streak by machining the grinding surface of the grinder stone 4, for instance.

The drawings and the related description are only intended to illustrate the idea of the invention. In its details, the invention can vary within the scope of the claims. In the figures and description, the method and measuring arrangement according to the solution are explained in association with a piston-loaded pulp grinder, but the presented solution can also be applied to other types of grinders, such as pulp grinders with a chain-feed structure. Although the example defines a situation where the temperature of the grinding surface 19 has on some sections risen above the normal temperature as abnormal, the solution can naturally be utilized in situations, in which the temperature of some section of the grinding surface 19 has sunk below the normal temperature. Such a situation can occur, for instance, when some section of the grinder stone is sharper than the rest of the grinder stone.

That which is claimed:

1. A method for monitoring the condition of a grinder stone of a pulp grinder, comprising determining a temperature profile for the grinding surface of the grinder stone substantially along the entire axial length of the grinder stone, determining a variable representing at least one piece of temperature data of the grinding surface of the grinder stone on the basis of said temperature profile, comparing the variable representing said temperature data with a reference variable corresponding to said temperature data and, if the variable representing said temperature data differs from said reference variable in a predefined manner, identifying the state relating to the condition of the grinder stone as abnormal on at least some section of the grinding surface.

2. A method as claimed in claim 1, wherein the state relating to the condition of the grinder stone is the temperature of the grinding surface of the grinder stone.

3. A method as claimed in claim 1, wherein the temperature profile for the grinding surface of the grinder stone is determined by measuring the temperature of water and/or a pulp suspension flowing between the grinding surface of the grinder stone and a finger plate arranged in the immediate vicinity of the grinding surface.

4. A method as claimed in claim 1, wherein the variable representing at least one piece of temperature data of the grinding surface of the grinder stone is the temperature of the grinding surface of the grinder stone measured by a single sensor and the reference variable corresponding to said temperature data is a predefined, fixed limit value corresponding to the highest allowable temperature of the grinding surface, whereby, if the temperature of the grinding surface of the grinder stone measured by a single sensor exceeds said limit value, an alarm signal is set and/or a procedure normalizing the state relating to the condition of the grinder stone is started.

5. A method as claimed in claim 1, wherein the variable representing at least one piece of temperature data of the grinding surface of the grinder stone is the temperature of the grinding surface of the grinder stone measured by a single sensor and the reference variable corresponding to said temperature data is the mean value of the temperatures measured by said temperature sensors, whereby, if the temperature of the grinding surface of the grinder stone measured by a single sensor exceeds said mean value by a predefined number, an alarm signal is set and/or a procedure normalizing the state relating to the condition of the grinder stone is started.

6. A method as claimed in claim 1, wherein the variable representing at least one piece of temperature data of the grinding surface of the grinder stone is the shape of the measured temperature profile and the reference variable is the shape of the temperature profile determined in a normal grinding situation, whereby, if the shape of the measured temperature profile differs from the shape of the temperature profile determined in a normal grinding situation by a predefined number, an alarm signal is set and/or a procedure normalizing the state relating to the condition of the grinder stone is started.

7. A method as claimed in any one of claims 4 to 6, wherein the procedure normalizing the state relating to the condition of the grinder stone is selected from the group consisting of i) water sharpening of a blunt part of the grinder stone, ii) cleaning, replacing or directioning of at least one washing nozzle, iii) cleaning, replacing or directioning of a sharpening nozzle, iv) fixing of a leak in the water sharpening system and v) mechanic removal of a burn streak on the grinding surface of the grinder stone by machining the grinding surface of the grinder stone.

8. A method as claimed in claim 1, wherein the variable representing at least one piece of temperature data of the grinding surface of the grinder stone is the difference between the highest and the lowest temperature value of the temperature profile or a variable representing deviation of the temperature profile.

9. A measuring arrangement for monitoring the condition of a grinder stone of a pulp grinder, the measuring arrangement comprising means for determining a temperature profile for the grinding surface of the grinder stone substantially along the entire axial length of the grinder stone, means for determining a variable representing at least one piece of temperature data of the grinding surface of the grinder stone on the basis of said temperature profile, means for comparing the variable representing said temperature data with a reference variable corresponding to said temperature data and means for identifying the state relating to the condition of the grinder stone as abnormal on at least some section of the grinding surface, if the variable representing the temperature data differs from said reference variable in a predefined manner.

10. A measuring arrangement as claimed in claim 9, wherein the state relating to the condition of the grinder stone is the temperature of the grinding surface of the grinder stone.

11. A measuring arrangement as claimed in claim 9, wherein, for determining the temperature profile for the grinding surface of the grinder stone, the measuring arrangement comprises contact elements arranged in connection with a finger plate arranged in the immediate vicinity of the grinding surface of the grinder stone, and temperature sensors in connection with the contact elements so that the temperature sensors are arranged to measure the temperature of the contact elements, which contact elements are arranged to substantially achieve the temperature of water and/or a pulp suspension flowing between the grinding surface and the finger plate, representing the temperature of the grinding surface.

12. A measuring arrangement as claimed in claim 11, wherein the contact elements are separated from the finger plate by means of insulating elements, preventing heat conduction between the finger plate and the contact elements.

13. A measuring arrangement as claimed in claim 9, wherein the variable representing at least one piece of temperature data of the grinding surface of the grinder stone is the temperature of the grinding surface of the grinder stone measured by a single sensor and the reference variable corresponding to said temperature data is a predefined, fixed limit value corresponding to the highest allowable temperature of the grinding surface, whereby, if the temperature of the grinding surface of the grinder stone measured by a single sensor exceeds said limit value, an alarm signal is arranged to be set and/or a procedure normalizing the state relating to the condition of the grinder stone is arranged to be started.

14. A measuring arrangement as claimed in claim 9, wherein the variable representing at least one piece of temperature data of the grinding surface of the grinder stone is the temperature of the grinding surface of the grinder stone measured by a single sensor and the reference variable corresponding to said temperature data is the mean value of the temperatures measured by said temperature sensors, whereby, if the temperature of the grinding surface of the grinder stone measured by a single sensor exceeds said mean value by a predefined number, an alarm signal is arranged to be set and/or a procedure normalizing the state relating to the condition of the grinder stone is arranged to be started.

15. A measuring arrangement as claimed in claim 9, wherein the variable representing at least one piece of temperature data of the grinding surface of the grinder stone is the shape of the measured temperature profile and the reference variable is the shape of the temperature profile determined in a normal grinding situation, whereby, if the shape of the measured temperature profile differs from the shape of the temperature profile determined in a normal grinding situation by a predefined number, an alarm signal is arranged to be set and/or a procedure normalizing the state relating to the condition of the grinder stone is arranged to be started.

16. A measuring arrangement as claimed in claim 9, wherein the variable representing at least one piece of temperature data of the grinding surface of the grinder stone is the difference between the highest and the lowest value of the temperature profile or a variable representing deviation of the temperature profile, whereby, if the difference between the highest and the lowest value of the temperature profile or the variable representing deviation of the temperature profile increases, an alarm signal is set and/or a procedure normalizing the state relating to the condition of the grinder stone is started.

17. A measuring arrangement as claimed in any one of claims 13 to 16, wherein the procedure normalizing the state relating to the condition of the grinder stone is selected from the group consisting of i) water sharpening of a blunt part of the grinder stone, ii) cleaning, replacing or directioning of at least one washing nozzle, iii) cleaning, replacing or directioning of a sharpening nozzle iv) fixing of a leak in the water sharpening system and v) mechanic removal of a burn streak on the grinding surface of the grinder stone by machining the grinding surface of the grinder stone.

\* \* \* \* \*